(12) United States Patent
Gotou et al.

(10) Patent No.: US 11,380,027 B2
(45) Date of Patent: Jul. 5, 2022

(54) MEDICAL IMAGE PROCESSING APPARATUS AND MEDICAL IMAGE PROCESSING METHOD

(71) Applicant: Hitachi, Ltd., Tokyo (JP)

(72) Inventors: Taiga Gotou, Tokyo (JP); Fuyuhiko Teramoto, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 148 days.

(21) Appl. No.: 16/887,494

(22) Filed: May 29, 2020

(65) Prior Publication Data

US 2021/0090307 A1 Mar. 25, 2021

(30) Foreign Application Priority Data

Sep. 24, 2019 (JP) .............................. JP2019-172532

(51) Int. Cl.
*G06K 9/00* (2022.01)
*G06T 11/00* (2006.01)
*G06T 7/20* (2017.01)
*G16H 30/40* (2018.01)

(52) U.S. Cl.
CPC .............. *G06T 11/008* (2013.01); *G06T 7/20* (2013.01); *G06T 11/006* (2013.01); *G16H 30/40* (2018.01); *G06T 2207/10081* (2013.01); *G06T 2207/30048* (2013.01); *G06T 2210/41* (2013.01)

(58) Field of Classification Search
CPC ................................................... G06T 11/008
See application file for complete search history.

(56) References Cited

U.S. PATENT DOCUMENTS

| 2011/0007956 | A1 | 1/2011 | Meyer et al. | |
| 2016/0134852 | A1* | 5/2016 | Gao | G06T 11/008 348/745 |
| 2016/0242726 | A1* | 8/2016 | Koehler | A61B 6/5205 |
| 2017/0301066 | A1* | 10/2017 | Wang | G06T 5/50 |
| 2019/0005686 | A1* | 1/2019 | Liu | G06T 5/002 |
| 2019/0206096 | A1* | 7/2019 | Fu | G06T 11/005 |
| 2020/0020140 | A1* | 1/2020 | Maltz | G06T 11/006 |

OTHER PUBLICATIONS

Y. Kyriakou et al., "Empirical beam hardening correction (EBHC) for CT", Med. Phys. 37 (10), Oct. 2010, pp. 5179-5187.

* cited by examiner

*Primary Examiner* — Oneal R Mistry
(74) *Attorney, Agent, or Firm* — Baker Botts L.L.P.

(57) ABSTRACT

There are provided a medical image processing apparatus and a medical image processing method making it possible to reduce metal artifacts with no loss of a detailed structure in a metallic region. The medical image processing apparatus is configured to reconstruct a tomographic image from projection data of a subject in which metal material is included and includes a projection space correction section which corrects the projection data and thereby generates corrected projection data, an image space correction section which corrects the tomographic image by using the corrected projection data, and a coefficient setting section which sets a projection space coefficient which is used in the projection space correction section and an image space coefficient which is used in the image space correction section.

9 Claims, 8 Drawing Sheets

MEDICAL IMAGE PROCESSING APPARATUS AND MEDICAL IMAGE PROCESSING METHOD

CLAIM OF PRIORITY

The present application claims priority from Japanese Patent Application JP 2019-172532 filed on Sep. 24, 2019, the content of which are hereby incorporated by references into this application.

BACKGROUND OF THE INVENTION

The present invention relates to a medical image processing apparatus and a medical image processing method which are adapted to handle a medical image which is obtained by a medical imaging apparatus such as an X-ray CT (Computed Tomography) apparatus and so forth.

BACKGROUND ART

The X-ray CT apparatus which is one example of the medical imaging apparatus acquires projection data at a plurality of projection angles by irradiating a subject with X rays which are emitted from various angles around the subject, backprojects the projection data and thereby reconstructs a tomographic image of the subject. The reconstructed tomographic image is used for an image diagnosis of the subject as a medical image. In a case where metal material such as a metal plate which is used for bone fixation is included in the subject, metal-induced artifacts, that is, so-called metal artifacts, are generated in the medical image and hinder the image diagnosis. A technology of reducing the metal artifacts which hinder the image diagnosis is called MAR (Metal Artifact Reduction), and various methods which use this technology are developed.

It is disclosed in U.S. Unexamined Patent Application Publication No. 2011/0007956 that a metallic region which is extracted on an original tomographic image is sequentially projected thereby to specify the metallic region on original projection data, and the original projection data is corrected by interpolating a projection value of the specified metallic region by using a projection value of a nonmetallic region. The method disclosed in U.S. Unexamined Patent Application Publication No. 2011/0007956 is called projection space correction because the original projection data is corrected.

In addition, it is disclosed in Yiannis Kyriakou, Esther Meyer, Daniel Prell, and Marc Kache Iriesz, "Empirical beam hardening correction (EBHC) for CT", Med. Phys. 37 (10), October 2010, 5179 that a high-density part which is extracted on an original tomographic image is sequentially projected thereby to obtain projection data of the high-density part and a plurality of base images which are obtained by reconstructing a combination of the projection data of the high-density part with original projection data are linearly coupled with the original tomographic image. The method disclosed in "Empirical beam hardening correction (EBHC) for CT" is called image space correction because the original tomographic image is corrected.

SUMMARY OF THE INVENTION

However, the methods disclosed in U.S. Unexamined Patent Application Publication No. 2011/0007956 and "Empirical beam hardening correction (EBHC) for CT" have both merits and demerits, and the medical image which is suited for the image diagnosis is not necessarily obtained by the abovementioned methods. Specifically, since in the projection space correction, the metallic region which is specified on the original projection data is interpolated by using the projection value of another (the nonmetallic) region, there are cases where a detailed structure in the metallic region may be lost. In addition, in the image space correction, in a case where saturation of the projection data of the high-density part occurs, for example, in a case where a metal-induced X-ray attenuation amount is too large, the metal artifacts are not sufficiently reduced.

Accordingly, the present invention aims to provide a medical image processing apparatus and a medical image processing method making it possible to reduce the metal artifacts with no loss of the detailed structure in the metallic region.

In order to attain the abovementioned aim, according to one embodiment of the present invention, there is provided a medical image processing apparatus which reconstructs a tomographic image from projection data of a subject in which metal material is included and includes a projection space correction section which corrects the projection data and thereby generates corrected projection data, an image space correction section which corrects the tomographic image by using the corrected projection data, and a coefficient setting section which sets a projection space coefficient which is used in the projection space correction section and an image space coefficient which is used in the image space correction section.

According to another embodiment of the present invention, there is also provided a medical image processing method for reconstructing a tomographic image from projection data of a subject in which metal material is included, including a projection space correcting step of correcting the projection data and thereby generating corrected projection data, an image space correcting step of correcting the tomographic image by using the corrected projection data, and a coefficient setting step of setting a projection space coefficient which is used in the projection space correcting step and an image space coefficient which is used in the image space correcting step.

According to the present invention, it is possible to provide the medical image processing apparatus and the medical image processing method making it possible to reduce the metal artifacts with no loss of the detailed structure in the metallic region.

DETAILED DESCRIPTION OF THE PREFERRED EMBODIMENTS

In the following, embodiments of a medical image processing apparatus and a medical image processing method according to the present invention will be described with reference to the appended drawings. Incidentally, in the following description and the appended drawings, the same numerals are assigned to the constitutional elements having the same functional configurations, and repetitive description thereof is omitted.

First Embodiment

Figure 1:
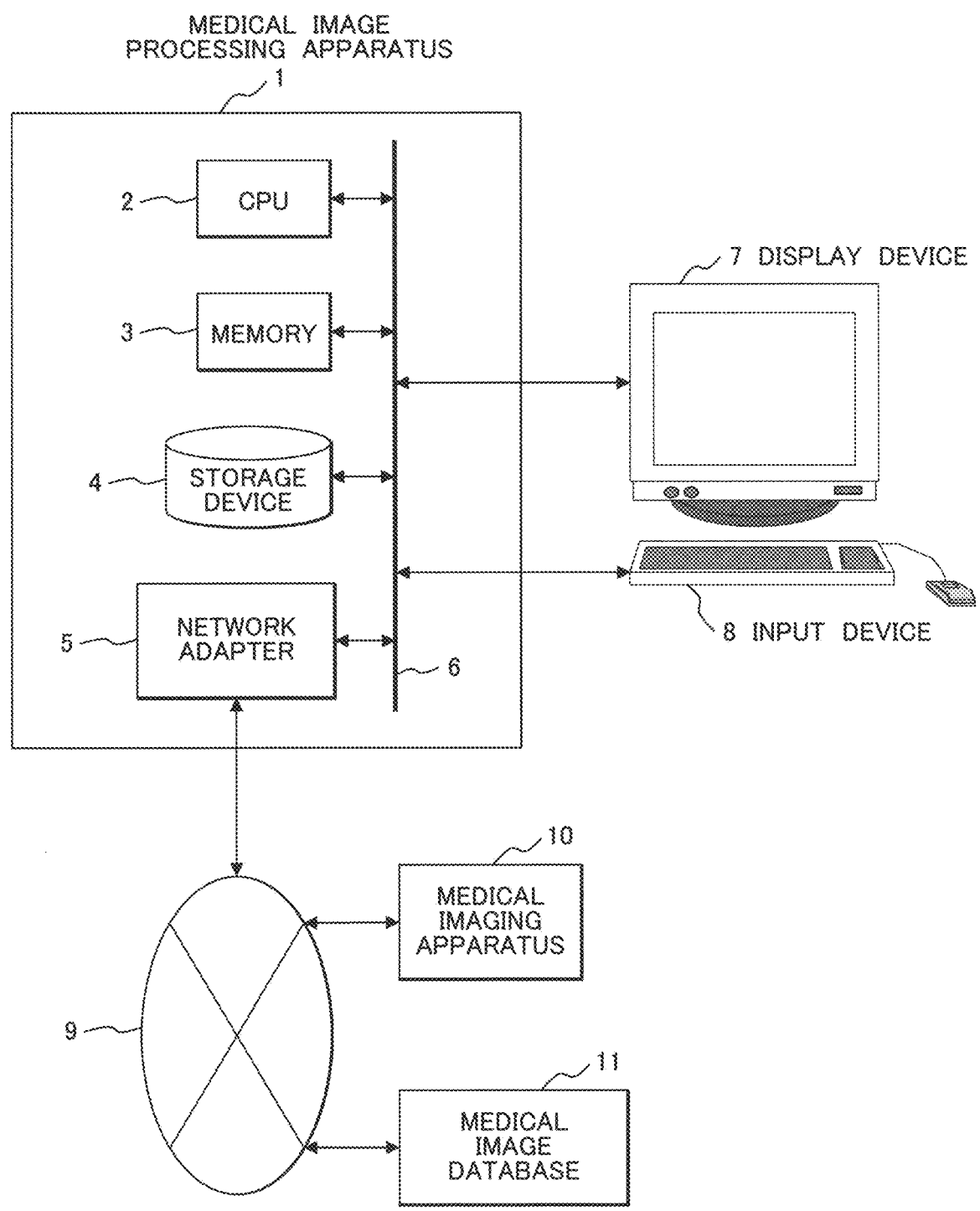
FIG. 1 is an overall configuration diagram illustrating one example of a medical image processing apparatus according to a first embodiment of the present invention.

FIG. 1 is a diagram illustrating one example of a hardware configuration of a medical image processing apparatus 1 according to the first embodiment of the present invention. The medical image processing apparatus 1 is configured such that a CPU (Central Processing Unit) 2, a memory 3, a storage device 4, and a network adapter 5 are connected with one another via a system bus 6 so as to freely transmit and receive signals. In addition, the medical image processing apparatus 1 is connected with a medical imaging apparatus 10 and a medical image database 11 over a network 9 so as to freely transmit and receive signals and is also connected with a display device 7 and an input device 8. Here, "to freely transmit and receive the signals" indicates a state of freely transmitting and receiving the signals electrically and optically mutually or from one to the other both in wired and wireless states.

The CPU 2 controls operations of respective constitutional elements. The CPU 2 loads a program and data which is necessary for execution of the program which are stored in the storage device 4 into the memory 3, executes the loaded program, and performs various types of image processing on a medical image. The memory 3 memorizes interim progress of the program and arithmetic processing that the CPU 2 executes. The storage device 4 stores the program that the CPU 2 executes and the data which is necessary for execution of the program, and is specifically an HDD (Hard Disk Drive), an SSD (Solid State Drive, and so forth. The network adapter 5 is adapted to connect the medical image processing apparatus 1 to the network 9 such as a LAN (Local Area Network), a telephone line, the Internet, and so forth. Various types of data that the CPU 2 handles may be transmitted to and received from the outside of the medical image processing apparatus 1 over the network 9 such as the LAN.

The display device 7 displays a result of processing and so forth that the medical image processing apparatus 1 executes and is specifically a liquid crystal display and so forth. The input device 8 is an operation device through which an operator gives operation instructions to the medical image processing apparatus 1 and is specifically a keyboard, a mouse, a touch panel, and so forth. The mouse may be other pointing devices such as a trackpad and a trackball.

Figure 2:
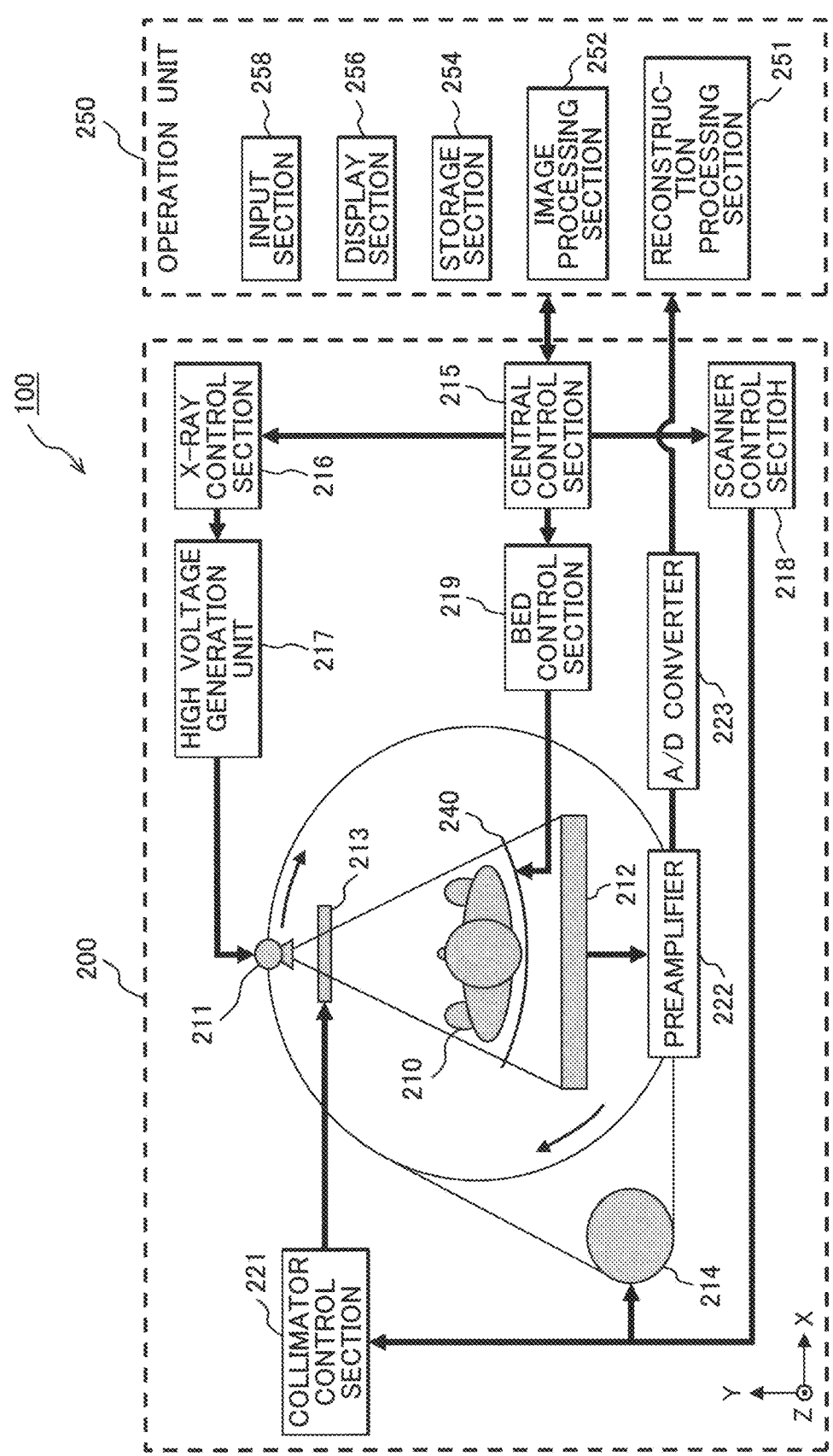
FIG. 2 is an overall configuration diagram illustrating one example of an X-ray CT apparatus which is one example of a medical imaging apparatus.

The medical imaging apparatus 10 is an X-ray CT (Computed Tomography) apparatus 100 which acquires, for example, projection data on a subject 210 and reconstructs a tomographic image from the projection data and will be described later by using FIG. 2. The medical image database 11 is a database system which stores the projection data, the tomographic image, and so forth which are acquired by the medical imaging apparatus 10.

An overall configuration of the X-ray CT apparatus 100 which is one example of the medical imaging apparatus 10 will be described by using FIG. 2. Incidentally, in FIG. 2, it is supposed that a lateral direction is an X-axis, a longitudinal direction is a Y-axis, and a direction which is vertical to a paper surface is a Z-axis. The X-ray CT apparatus 100 includes a scanner 200 and an operation unit 250. The scanner 200 has an X-ray tube 211, a detector 212, a collimator 213, a drive section 214, a central control section 215, an X-ray control section 216, a high voltage generation section 217, a scanner control section 218, a bed control section 219, a collimator control section 221, a preamplifier 222, an A/D converter 223, a bed 240, and so forth.

The X-ray tube 211 irradiates the subject 210 who is laid down on the bed 240 with X rays. A high voltage that the high voltage generation section 217 generates is applied to the X-ray tube 211 and thereby the subject 210 is irradiated with the X rays which are emitted from the X-ray tube 211 in accordance with a control signal which is transmitted from the X-ray control section 216.

The collimator 213 restricts a range which is irradiated with the X rays which are emitted from the X-ray tube 211. The X-ray irradiation range is set in accordance with a control signal which is transmitted from the collimator control section 221.

The detector 212 detects the X rays which transmit through the subject 210 and thereby measures a spatial distribution of the transmitted X-rays. The detector 212 is disposed so as to face the X-ray tube 211, and many detection elements are two-dimensionally arrayed in a plane which faces the X-ray tube 211. A signal which is measured by the detector 212 is amplified by the preamplifier 222 and then is converted into a digital signal by the A/D converter 223. Then, various types of correction processing are performed on the digital signal, and thereby projection data is acquired.

The drive section 214 drives the X-ray tube 211 and the detector 212 so as to rotate around the subject 210 in accordance with a control signal which is transmitted from the scanner control section 218. X-ray irradiation and detection are performed in association with rotation of the X-ray tube 211 and the detector 212, and thereby the projection data which is collected from a plurality of projection angles is acquired. A data collection unit per projection angle is called view. In arrangement of the respective detection elements of the detector 212 which are two-dimensionally arrayed, a rotation direction of the detector 212 is called a channel and a direction which is orthogonal to the channel is called a column. The projection data is identified on the basis of the view, the channel, and the column.

The bed control section 219 controls an operation of the bed 240 so as to maintain the bed 240 in a stationary state and/or to move the bed 240 in the Z-axis direction at a constant velocity while the X-ray irradiation and detection are being performed. A scan which is performed in a state of maintaining the bed 240 in the stationary state is called an axial scan and a scan which is performed while moving the bed 240 is called a spiral scan respectively.

The central control section 215 controls the above-described operations of the scanner 200 in accordance with instructions from the operation unit 250. Next, the operation unit 250 will be described. The operation unit 250 has a reconstruction processing section 251, an image processing section 252, a storage section 254, a display section 256, an input section 258, and so forth.

The reconstruction processing section 251 reconstructs the tomographic image by backprojecting the projection data that the scanner 200 acquires. The image processing section 252 performs various types of image processing for making the tomographic image into an image which is suitable for a diagnose. The storage section 254 stores the projection data, the tomographic image, and the image which is obtained after execution of the image processing. The display section 256 displays the tomographic image and the image which is obtained after execution of the image processing. The input section 258 is used in a case where the operator sets scanning conditions (a tube voltage, a tube current, a scanning speed, and so forth) used when acquiring the projection data of the subject 210 and tomographic image reconstruction conditions (a reconstruction filter, an FOV (Field Of View) size, and so forth).

Incidentally, the operation unit 250 may be the medical image processing apparatus 1 which is illustrated in FIG. 1. In this case, the reconstruction processing section 251 and the image processing section 252 correspond to the CPU 2, the storage section 254 corresponds to the storage device 4, the display section 256 corresponds to the display device 7, and the input section 258 corresponds to the input device 8, respectively.

Figure 3:
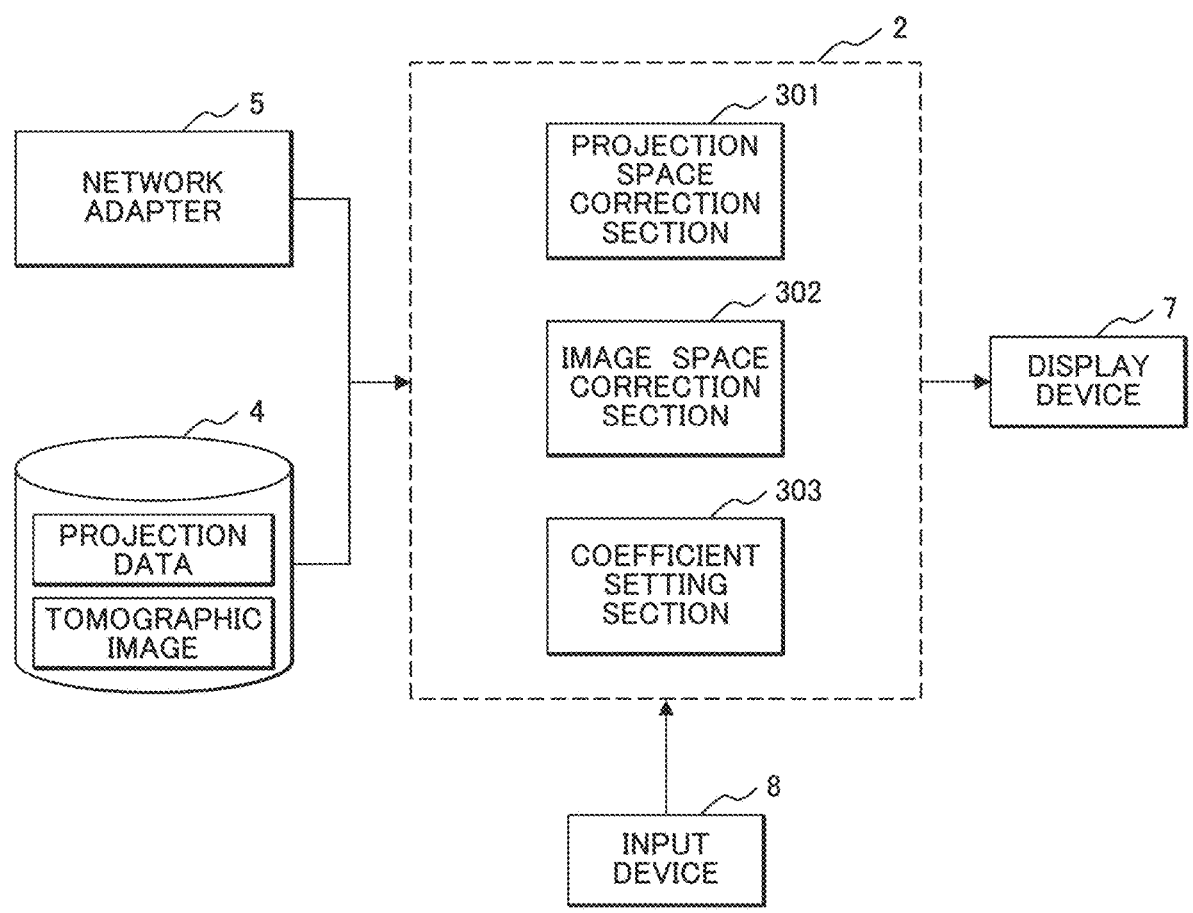
FIG. 3 is a functional block diagram illustrating one example of the medical image processing apparatus.

Essential parts of the medical image processing apparatus 1 according to the first embodiment will be described by using FIG. 3. Incidentally, the essential parts may be configured by either dedicated hardware or software which operates on the CPU 2. In the following, a case where the essential parts according to the first embodiment are configured by the software will be described.

The medical image processing apparatus 1 according to the first embodiment includes a projection space correction section 301, an image space correction section 302, and a coefficient setting section 303 which operate on the CPU 2. In addition, the tomographic image and the projection data which are generated by the X-ray CT apparatus 100 are stored in the storage device 4. In the following, respective components will be described.

The projection space correction section 301 corrects the projection data of the subject 210 which includes metal material and thereby generates corrected projection data. Specifically, the corrected projection data is generated by using metal projection data which is obtained by sequentially projecting a metal image in which a metallic region is extracted, nonmetal projection data which is obtained by interpolating a projection value of the metallic region which is specified on the projection data by using a projection value of a nonmetallic region, a projection space coefficient to be described later, and so forth.

The image space correction section 302 corrects the tomographic image of the subject 210 by using the corrected projection data that the projection space correction section 301 generates. Specifically, the tomographic image of the subject 210 is corrected by using a base image which is reconstructed from the projection data of the subject 210 and base projection data which is generated by combining the nonmetal projection data with the metal projection data, the corrected projection data, an image space coefficient to be described later, and so forth.

The coefficient setting section 303 sets the projection space coefficient that the projection space correction section 301 uses and the image space coefficient that the image space correction section 302 uses. Specifically, the projection space coefficient and the image space coefficient are set by the coefficient setting section 303 on the basis of any of a feature value of the metal material which is included in the subject 210, the scanning condition concerned used when acquiring the projection data of the subject 210, and the reconstruction condition concerned used when reconstructing the tomographic image of the subject 210.

Figure 4:
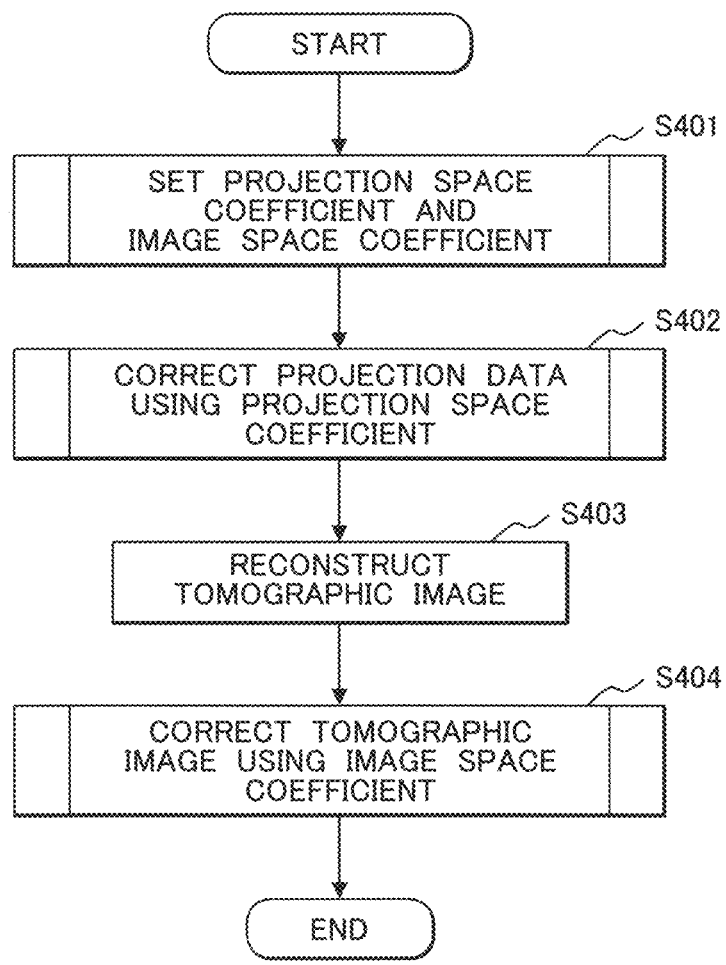
FIG. 4 is a diagram illustrating one example of a flow of processing of a medical image processing method.

One example of a flow of processing which is executed by the medical image processing apparatus 1 according to the first embodiment will be described by using FIG. 4.

(S401)

The coefficient setting section 303 sets the projection space coefficient and the image space coefficient. The projection space coefficient and the image space coefficient are set on the basis of any of the feature value of the metal material which is included in the subject 210, the scanning condition concerned which is used when acquiring the projection data of the subject 210, and the reconstruction condition concerned which is used when reconstructing the tomographic image of the subject 210.

Figure 5:
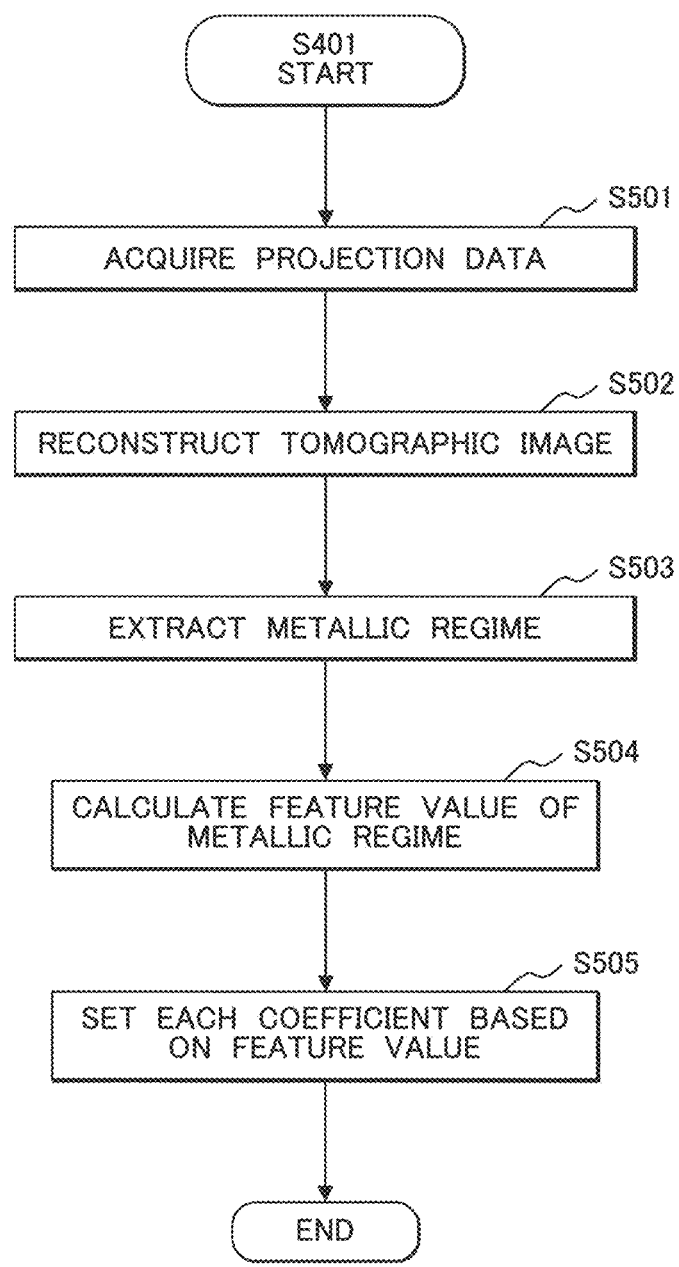
FIG. 5 is a diagram illustrating one example of a flow of a process in the coefficient setting step in the first embodiment of the present invention.

One example of a flow of a process in S401 will be described by using FIG. 5. In the first embodiment, the projection space coefficient and the image space coefficient are set on the basis of the feature value of the metal material which is included in the subject 210.

(S501)

The coefficient setting section 303 acquires projection data $P_{org}$ of the subject 210 which includes the metal material. The projection data $P_{org}$ is read out of the storage device 4 and/or transmitted from the outside via the network adapter 5.

(S502)

Figure 6:
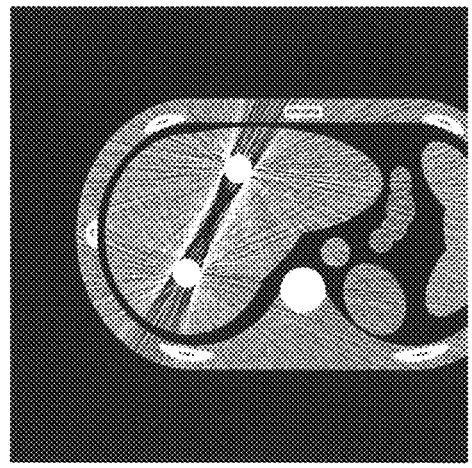
FIG. 6 is a diagram illustrating one example of a metal artifact.

The coefficient setting section 303 reconstructs a tomographic image $F_{org}$ from the projection data $P_{org}$. A metal artifact is generated in the tomographic image $F_{org}$ under the influence of the metal material. One example of the metal artifact is illustrated in FIG. 6. FIG. 6 illustrates one example of a tomographic image which is obtained by scanning an abdominal phantom and in which a dark band is generated between tow metallic regions which are present in the liver, and streak artifacts which extend starting from the respective metallic regions are generated.

(S503)

The coefficient setting section 303 extracts the metallic region from within the tomographic image $F_{org}$ and thereby generates a metal image $F_{mtl}$. Thresholding is used for extraction of the metallic region. In a case where, for example, 2000 HU (Hounsfield Unit) is set as a threshold value, a pixel having a pixel value which exceeds 2000 HU is extracted as the metallic region on the tomographic image $F_{org}$. The threshold value used for the thresholding may be set to a larger value as a maximum pixel value of the tomographic image $F_{org}$ becomes larger. A pixel value which corresponds to a soft tissue is subtracted from a pixel value of the extracted metallic region, a pixel value which corresponds to air, for example, −1000 HU is set as a threshold value of a pixel value of a region other than the metallic region, and thereby the metal image $F_{mtl}$ is generated. It becomes possible to avoid excessive enlargement of a projection value of first order corrected projection data to be described later by subtracting the pixel value of the soft tissue from the pixel value of the metallic region. The coefficient setting section 303 may generate the metal projection data $P_{mtl}$ by sequentially projecting the metal image $F_{mtl}$.

(S504)

The coefficient setting section 303 calculates the feature value of the metallic region by using the metal image $F_{mtl}$. One of a maximum pixel value $v_{mtl\_max}$, an area $v_{mtl\_area}$, and roundness $v_{mtl\_shp}$ of the metallic region is included in the feature value of the metallic region.

The maximum pixel value $v_{mtl\_max}$ of the metallic region is obtained by extracting a maximum value from within the pixel values of the metal image $F_{mtl}$.

The area $v_{mtl\_area}$ of the metallic region is obtained by counting the number of pixels in the metallic region and multiplying a per-pixel area by the counted number of the pixels. Incidentally, in a case where the plurality of metallic regions are present, a total area of the metallic regions is obtained by adding up the numbers of pixels which are counted in the respective metallic regions and multiplying the added-up number of pixels by the per-pixel area.

The roundness $v_{mtl\_shp}$ of the metallic region is obtained by dividing a minor axis of the metallic region by a major axis of the metallic region. The smaller a difference between the major axis and the minor axis is, the larger the roundness $v_{mtl\_shp}$ is, and the larger the difference between the major axis and the minor axis is, the smaller the roundness $v_{mtl\_shp}$ is. Incidentally, in a case where the plurality of metallic regions are present, the minor axis and the major axis are obtained by regarding the plurality of metallic regions as one metallic region. That is, also each distance between the respective metallic regions concerned is included, and then the minor axis and the major axis are obtained.

The roundness $v_{mtl\_shp}$ of the metallic region may also be obtained by using the metal projection data $P_{mtl}$. In a case where the metal projection data $P_{mtl}$ is used, the roundness $v_{mtl\_shp}$ is obtained by the following formula.

$$v_{mtl\_shp} = \frac{A_{min}(d(\text{view}, \text{slice}))}{A_{max}(d(\text{view}, \text{slice}))} \quad \text{[Numerical Formula 1]}$$

$$d(\text{view}, \text{slice}) = \sqrt{\frac{\sum_{ch}(ch - g(\text{view}, \text{slice}))^2 P_{mtl}(\text{view}, \text{slice}, ch)}{\sum_{ch} P_{mtl}(\text{view}, \text{slice}, ch)}}$$

$$g(\text{view}, \text{slice}) = \frac{\sum_{ch} ch \cdot P_{mtl}(\text{view}, \text{slice}, ch)}{\sum_{ch} P_{mtl}(\text{view}, \text{slice}, ch)}$$

Here, $A_{min}(\ )$ is an operator used for obtaining a minimum value, $A_{max}(\ )$ is an operator used for obtaining a maximum value, view is a view position, slice is a column position, and ch is a channel position. In addition, d(view, slice) is a channel-direction dispersion of the projection values of view, slice in the metal projection data $P_{mtl}$, and g(view, slice) is a gravity center channel of the projection values of view, slice in the metal projection data $P_{mtl}$.

The coefficient setting section 303 sets a projection space coefficient $\beta_{raw}$ and an image space coefficient $\beta_{img}$ on the basis of the feature value of the metallic region. The projection space coefficient $\beta_{raw}$ is obtained by, for example, the following formula.

$$\beta_{raw} = \gamma \cdot (\lambda \cdot v_{mtl\_max} + \mu \cdot v_{mtl\_area} + \xi \cdot v_{mtl\_shp}) \quad \text{[Numerical Formula 2]}$$

In addition, the image space coefficient $\beta_{img}$ is obtained by, for example, the following formula.

$$\beta_{img} = \rho - \beta_{raw} \quad \text{[Numerical Formula 3]}$$

Here, $\gamma$ is an operator-settable variable, $\lambda$, $\rho$, $\xi$, and $\rho$ are positive constants. The variable $\gamma$ is set by the operator through the input device 8. The constants $\lambda$, $\mu$, $\xi$, and $\rho$ are empirically set in advance on the basis of a result of scanning of a phantom which includes the metal material whose shape and attenuation coefficient are already known. The projection space coefficient $\beta_{raw}$ is transmitted to the projection space correction section 301 and the image space coefficient $\beta_{img}$ is transmitted to the image space correction section 302.

According to the numerical formula 2, the larger any of the maximum pixel value $v_{mtl\_max}$, the area $v_{mtl\_area}$, and the roundness $v_{mtl\_shp}$ which are the feature values of the metallic region is, the larger the projection space coefficient $\beta_{raw}$ becomes. In addition, according to the numerical formula 3, the larger the projection space coefficient $\beta_{raw}$ is, the smaller the image space coefficient $\beta_{img}$ becomes. That is, the larger the feature value concerned of the metallic region is, the more a projection space correction ratio in which the original projection data is corrected is increased than an image space correction ratio in which the original tomographic image is corrected. In a case where the feature value concerned of the metallic region is large, it is possible to sufficiently reduce the metal artifacts which are not sufficiently reduced by the image space correction by increasing the projection space correction ratio.

Further, in a case where the image space coefficient $\beta_{img}$ is uniquely determined, for example, in a case where the method disclosed in "Empirical beam hardening correction (EBHC) for CT" is used, the projection space coefficient $\beta_{raw}$ may be set on the basis of the numerical formula 3. In addition, according to the numerical formula 2, it is possible for the operator to freely set the projection space coefficient $\beta_{raw}$ while comparing images which are obtained before correction and after correction with each other by adjusting the variable $\gamma$.

Description will be made by returning to FIG. 4.

(S402)

Figure 7:
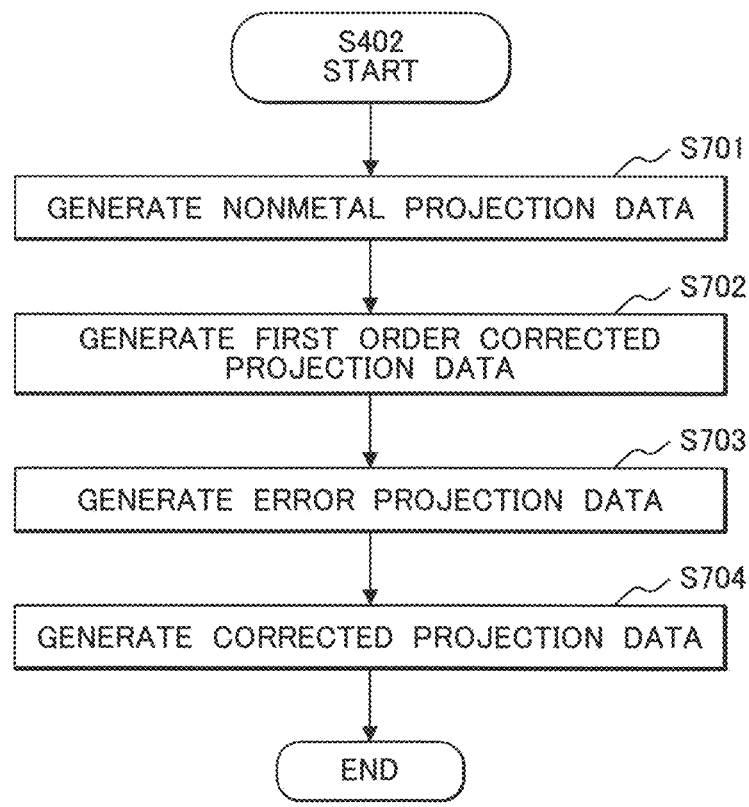
FIG. 7 is a diagram illustrating one example of a flow of a process in the projection space correcting step.

The projection space correction section 301 corrects the projection data $P_{org}$ by using the projection space coefficient $\beta_{raw}$. One example of a flow of a process in the step S402 will be described by using FIG. 7.

(S701)

The projection space correction section 301 generates nonmetal projection data $P_{lin}$ in the following procedure. First, the projection space correction section 301 specifies the metallic region on the projection data $P_{org}$ on the subject 210 by using metal projection data $P_{mtl}$ which is generated by sequentially projecting the metal image $F_{mtl}$. Next, the projection space correction section 301 replaces the projection value of the metallic region which is specified on the projection data $P_{org}$ with a value which is obtained by interpolating the projection value by using projection values of nonmetallic regions which are adjacent to the metallic region. In short, the projection space correction section 301 obtains a mean value of the projection values of the two nonmetallic regions which are adjacent to the metallic region in the channel direction and replaces the projection value of the metallic region with the obtained mean value. In another example, the projection space correction section 301 replaces the projection value of the metallic region with a value which is obtained by linearly interpolating the projection value by using projection values of nonmetallic regions which are adjacent to the metallic region in the channel direction and the column direction. The nonmetal projection data $P_{lin}$ in which the metallic region is not included is generated by such replacement using an interpolated value as described above. Not only the metallic region is not included in the nonmetal projection data $P_{lin}$ but also artifact components which are generated under the influence of the metal material are reduced in the nonmetal projection data $P_{lin}$.

(S702)

The projection space correction section 301 generates first order corrected projection data $P_{fst\_c}$ by adding the nonmetal projection data $P_{lin}$ and the metal projection data $P_{mtl}$ together. Since the nonmetal projection data $P_{lin}$ in which the metal artifact components are reduced and the metal projection data $P_{mtl}$ which includes the projection value of the metallic region are added together, the first order corrected projection data $P_{fst\_c}$ becomes projection data in which the metal artifacts are reduced while including the projection value of the metallic region. Incidentally, since the pixel value of the soft tissue is subtracted from the pixel value of the metallic region in S503, the projection value of the metallic region on the first order corrected projection data $P_{fst\_c}$ does not reach an extremely large value.

(S703)

The projection space correction section 301 generates error projection data $P_{err}$ by subtracting the first order corrected projection data $P_{fst\_c}$ from the projection data $P_{org}$ of the subject 210. Since the first order corrected projection data $P_{fst\_c}$ in which the metal artifacts are reduced is subtracted from the original projection data $P_{org}$, the error projection data $P_{err}$ becomes projection data in which the metal artifact is contained as the main component.

(S704)

The projection space correction section 301 corrects the projection data $P_{org}$ by using the error projection data $P_{err}$ and the projection space coefficient $\beta_{raw}$ and thereby generates corrected projection data $P_{corr}$. The corrected projection data $P_{corr}$ is generated by, for example, the following formula.

$$P_{corr}=P_{org}-\beta_{raw} \cdot P_{err} \quad \text{[Numerical Formula 4]}$$

Incidentally, correction of the projection data $P_{org}$ is not limited to the correction using the numerical formula 4, for example, the first order corrected projection data $P_{fst\_c}$ which is generated in S702 may be used in place of the corrected projection data $P_{corr}$, and the projection data $P_{org}$ may be corrected by a well-known method such as the method disclosed in "Empirical beam hardening correction (EBHC) for CT".

Description will be made by retuning to FIG. 4.

(S403)

The CPU 2 or the reconstruction processing section 251 reconstructs a tomographic image $F_{raw\_corr}$ from the corrected projection data $P_{corr}$ which is generated in step S402.

(S404)

Figure 8:
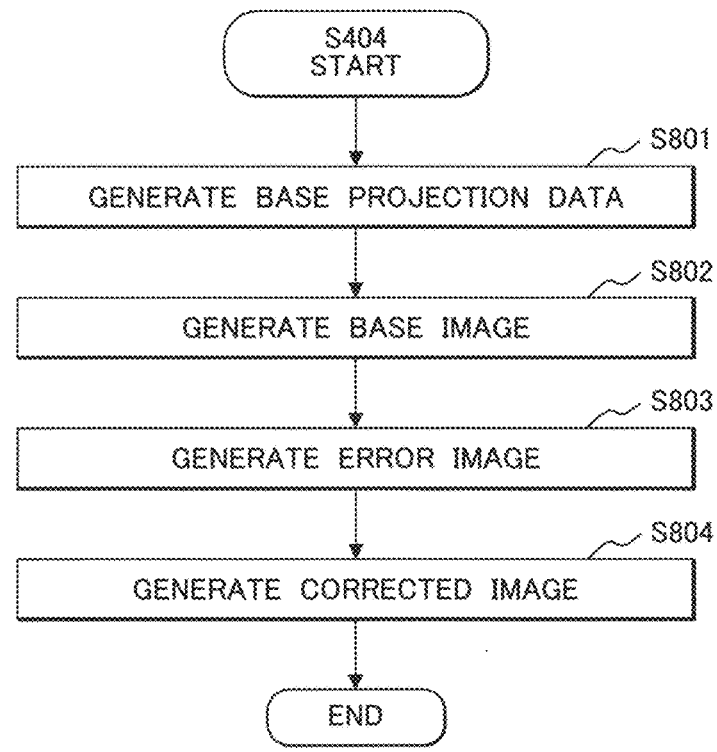
FIG. 8 is a diagram illustrating one example of a flow of a process in the image space correcting step.

The image space correction section 302 corrects the tomographic image $F_{raw\_corr}$ by using the projection space coefficient $\beta_{img}$. One example of a flow of a process in step S404 will be described by using FIG. 8.

(S801)

The image space correction section 302 generates base projection data $P_{base}$ which serves as the base of the metal artifact. The base projection data $P_{base}$ is generated by, for example, the following formula as data which is subjected to series expansion by the nonmetal projection data $P_{lin}$ and the metal projection data $P_{mtl}$ or by the projection data $P_{org}$ and the metal projection data $P_{mtl}$.

$$P_{base}=P_{lin}^{m} \cdot P_{mtl}^{n} \text{ or}$$

$$P_{base}=P_{org}^{m} \cdot P_{mtl}^{n}[ \quad \text{[Numerical Formula 5]}$$

Here, m and n are integers and a combination of m with n is set depending on a necessary correction accuracy and an allowable arithmetic operation time and, for example, (m, n)=(1, 1), (0, 2) is set.

(S802)

The image space correction section 302 generates a base image $F_{base}$ by using the base projection data $P_{base}$. The base image $F_{base}$ is reconstructed from the base projection data $P_{base}$ and is generated in accordance with the number of pieces of the base projection data $P_{base}$ which are generated in S801. That is, in a case where the number of pieces of the base projection data $P_{base}$ is L, the number of the base images $F_{base}$ is L. For example, in a case where (m, n)=(1, 1), (0, 2) is set, L=2.

(S803)

The image space correction section 302 generates an error image $F_{err}$ by subjecting the base images $F_{base}$ to weighted addition. The error image $F_{err}$ is generated by, for example, the following formula.

$$F_{err} = \sum_{l=1}^{L} w(l) \cdot F_{base}(l) \quad \text{[Numerical Formula 6]}$$

Here, w(1) is a first-item weighting coefficient and is empirically set in advance on the basis of the result of scanning of the phantom which includes the metal material whose shape and attenuation coefficient are already known and/or is calculated by a sequential solution.

(S804)

The image space correction section 302 corrects the tomographic image $F_{raw\_corr}$ by using the error image $F_{err}$ and the image space coefficient $\beta_{img}$ and thereby generates a corrected image $F_{img\_corr}$. The corrected image $F_{img\_corr}$ is generated by, for example, the following formula.

$$F_{img\_corr}=F_{raw\_corr}-\beta_{img} \cdot F_{err} \quad \text{[Numerical Formula 7]}$$

Incidentally, correction of the tomographic image $F_{raw\_corr}$ is not limited to the correction using the numerical formula 7 and the tomographic image $F_{raw\_corr}$ may be corrected by the well-known method such as the method disclosed in "Empirical beam hardening correction (EBHC) for CT".

Since the projection space coefficient $\beta_{raw}$ and the image space coefficient $\beta_{img}$ are set on the basis of the feature value concerned of the metallic region along the flow of the above-described process, it is possible to reduce the metal artifacts with no loss of a detailed structure in the metallic region.

Second Embodiment

In the first embodiment, it is described that the projection space coefficient $\beta_{raw}$ and the image space coefficient $\beta_{img}$ are set on the basis of any one of the feature values of the metallic region. In the second embodiment, description will be made in regard to the point that the projection space coefficient $\beta_{raw}$ and the image space coefficient $\beta_{img}$ are set on the basis of a scanning condition, in particular, on the basis of a cone angle which is an opening angle of a projection line which runs in a body-axis direction of the subject 210. Incidentally, since the second embodiment is different from the first embodiment only in the flow of the process in S401 in FIG. 4, description about other points is omitted.

Figure 9:
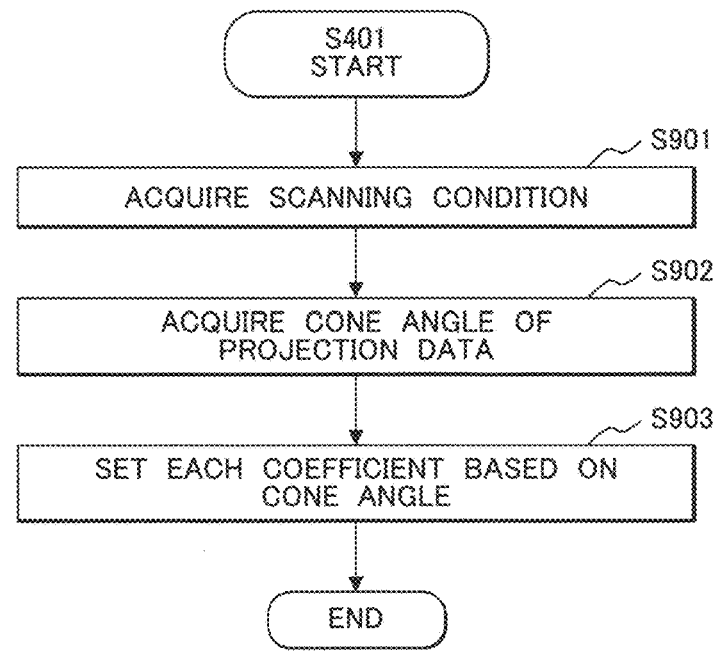
FIG. 9 is a diagram illustrating one example of a flow of a process in the coefficient setting step according to a second embodiment of the present invention.

One example of a flow of a process of setting the projection space coefficient $\beta_{raw}$ and the image space coefficient $\beta_{img}$ in the second embodiment will be described by using FIG. 9.

(S901)

The coefficient setting section 303 acquires the scanning condition. The scanning condition is read out of the storage device 4 and/or transmitted from the outside via the network adapter 5.

(S902)

The coefficient setting section 303 acquires the cone angle of each projection value of the projection data $P_{org}$ on the basis of the scanning condition. The cone angle is the opening angle of the projection line which runs in the body axis direction of the subject 210 and is determined on the basis of a channel position and a column position of each projection value.

(S903)

The coefficient setting section 303 sets the projection space coefficient $\beta_{raw}$ and the image space coefficient $\beta_{img}$ on the basis of the cone angle of each projection value. Specifically, the smaller the cone angle is, the larger the projection space coefficient $\beta_{raw}$ is set and the smaller the image space coefficient $\beta_{img}$ is set. In a case where the cone angle is large, since an error which would occur when generating the metal projection data $P_{mtl}$ by sequentially projecting the metal image $F_{mtl}$ in projection space correction becomes large, image deterioration caused by the projection space correction is suppressed by setting the projection space coefficient $\beta_{raw}$ small.

Since the projection space coefficient $\beta_{raw}$ and the image space coefficient $\beta_{img}$ are set on the basis of the scanning condition, in particular, on the basis of the cone angle which is the opening angle of the projection line which runs in the body-axis direction of the subject 210 along the flow of the above-described process, it is possible to reduce the metal artifacts with no loss of the detailed structure in the metallic region.

Third Embodiment

In the first embodiment, it has been described that the projection space coefficient $\beta_{raw}$ and the image space coefficient $\beta_{img}$ are set on the basis of the feature value concerned of the metallic region. In the third embodiment, description will be made with regard to the point that the projection space coefficient $\beta_{raw}$ and the image space coefficient $\beta_{img}$ are set on the basis of the magnitude of body motion of the subject 210 when scanning the projection data $P_{org}$. Incidentally, since the third embodiment is different from the first embodiment only in the flow of the process in S401 in FIG. 4, the description about other points is omitted.

Figure 10:
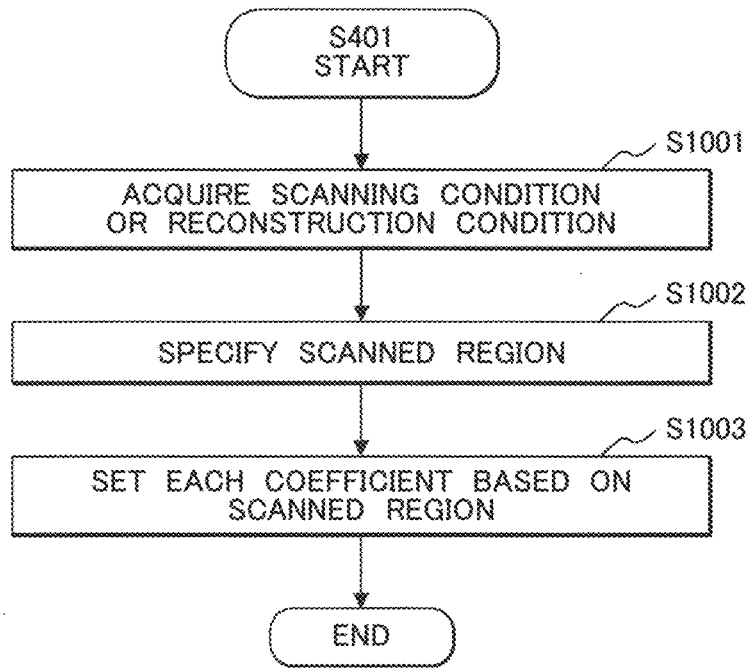
FIG. 10 is a diagram illustrating one example of a flow of a process in the coefficient setting step according to a third embodiment of the present invention.

One example of a flow of a process of setting the projection space coefficient $\beta_{raw}$ and the image space coefficient $\beta_{img}$ in the third embodiment will be described by using FIG. 10.

(S1001)

The coefficient setting section 303 acquires the scanning condition concerned or the reconstruction condition concerned. The scanning condition concerned or the reconstruction condition concerned is read out of the storage device 4 and/or is transmitted from the outside via the network adaptor 5.

(S1002)

The coefficient setting section 303 specifies a scanned region where the projection data $P_{org}$ is scanned on the basis of the scanning condition concerned or the reconstruction condition concerned. Specifically, in a case where electrocardiogram-gated scanning or electrocardiogram-gated reconstruction is being performed or in a case where a reconstruction filter for the heart and lung fields is selected, it is specified that the scanned region is the heart or the chest.

(S1003)

The coefficient setting section 303 sets the projection space coefficient $\beta_{raw}$ and the image space coefficient $\beta_{img}$ on the basis of the scanned region. Specifically, in a case where the scanned region is a region which is large in body motion just like the heart or the chest, the projection space coefficient $\beta_{raw}$ is set small and the image space coefficient $\beta_{img}$ is set large. In addition, in a case where the scanned region is a region which is small in body motion just like the head, the projection space coefficient $\beta_{raw}$ is set large and the image space coefficient $\beta_{img}$ is set small. In a case where the body motion is large, since the error which would occur when generating the metal projection data $P_{mtl}$ by sequentially projecting the metal image $F_{mtl}$ in the projection space correction becomes large, the image deterioration caused by the projection space correction is suppressed by setting the projection space coefficient $\beta_{raw}$ small.

Since the projection space coefficient $\beta_{raw}$ and the image space coefficient $\beta_{img}$ are set on the basis of the magnitude of the body motion of the scanned region along the flow of the above-described process, it is possible to reduce the metal artifacts with no loss of the detailed structure in the metallic region.

Figure 11:
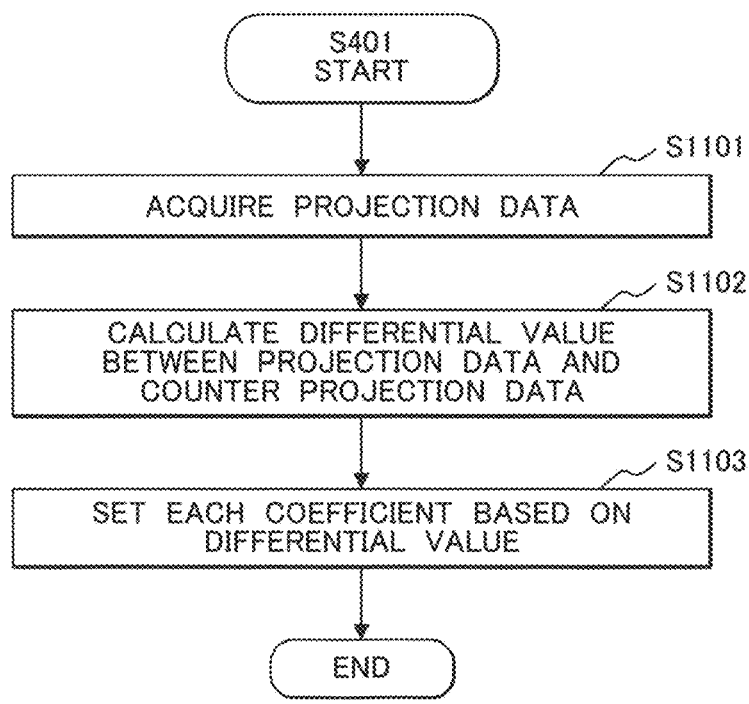
FIG. 11 is a diagram illustrating another example of the flow of the process in the coefficient setting step according to the third embodiment of the present invention.

Another example of the flow of the process of setting the projection space coefficient $\beta_{raw}$ and the image space coefficient $\beta_{img}$ in the third embodiment will be described by using FIG. 11.

(S1101)

The coefficient setting section 303 acquires the projection data $P_{org}$ of the subject 210 which includes the metal material. The projection data $P_{org}$ is read out of the storage device 4 and/or is transmitted from the outside via the network adaptor 5.

(S1102)

The coefficient setting section 303 calculates a differential value between the projection data $P_{org}$ and projection data which is opposed to the projection data $P_{org}$, that is, counter projection data which is different from the projection data $P_{org}$ in projection angle by 180 degrees. Since the counter projection data is obtained by scanning the region where the projection data $P_{org}$ is scanned from an opposite direction, in a case where no body motion takes place, the differential value is reduced to zero and an absolute value of the differential value is increased as the body motion becomes large.

(S1103)

The coefficient setting section 303 sets the projection space coefficient $\beta_{raw}$ and the image space coefficient $\beta_{img}$ on the basis of the absolute value of the differential value. Specifically, in a case where the absolute value of the differential value is large, the projection space coefficient $\beta_{raw}$ is set large and the image space coefficient $\beta_{img}$ is set small. In a case where the absolute value of the differential value which indicates the magnitude of the body motion is large, since the error which would occur when generating the metal projection data $P_{mtl}$ by sequentially projecting the metal image $F_{mtl}$ in the projection space correction becomes large, the image deterioration caused by the projection space correction is suppressed by setting the projection space coefficient $\beta_{raw}$ small.

Since the projection space coefficient $\beta_{raw}$ and the image space coefficient $\beta_{img}$ are set on the basis of the magnitude of the body motion of the scanned region also along the flow of the above-described process, it is possible to reduce the metal artifacts with no loss of the detailed structure in the metallic region.

Incidentally, the medical image processing apparatus and the medical image processing method of the present invention are not limited to the above-described embodiments and may be embodied by modifying the constitutional elements within the range not deviating from the gist of the present invention. In addition, the plurality of the constitutional elements which are disclosed in the abovementioned embodiments may be mutually combined appropriately. For example, configurations of the first to third embodiments may be mutually combined so as to set the projection space coefficient $\beta_{raw}$ and the image space coefficient $\beta i_{mg}$ on the basis of the feature value(s) of the metallic region, the cone angle, and the magnitude of the body motion. Further, some constitutional elements may be deleted from all the constitutional elements described in the abovementioned embodiments.

REFERENCE SIGNS LIST

1: medical image processing apparatus, 2: CPU, 3: memory, 4: storage device, 5: network adapter, 6: system bus, 7: display device, 8: input device, 10: medical imaging apparatus, 11: medical image database, 100: X-ray CT apparatus, 200: scanner, 210: subject, 211: X-ray tube, 212: detector, 213: collimator, 214: drive section, 215: central control section, 216: X-ray control section, 217: high voltage generation section, 218: scanner control section, 219: bed control section, 221: collimator control section, 222: preamplifier, 223: A/D converter, 240: bed, 250: operation unit, 251: reconstruction processing section, 252: image processing section, 254: storage section, 256: display section, 258: input section, 301: projection space correction section, 302: image space correction section, 303: coefficient setting section

What is claimed is:

1. A medical image processing apparatus which reconstructs a tomographic image from projection data of a subject in which metal material is included, comprising:
   a projection space correction section which corrects the projection data and thereby generates corrected projection data;
   an image space correction section which corrects the tomographic image by using the corrected projection data; and
   a coefficient setting section which sets a projection space coefficient which is used in the projection space correction section and an image space coefficient which is used in the image space correction section,
   wherein the larger the projection space coefficient is, the smaller the image space coefficient becomes.

2. The medical image processing apparatus according to claim 1, wherein the coefficient setting section sets the projection space coefficient and the image space coefficient on the basis of any of a feature value of a metallic region, a scanning condition used when acquiring the projection data, and a reconstruction condition used when reconstructing the tomographic image.

3. The medical image processing apparatus according to claim 2,
   wherein the feature value includes any of a maximum pixel value, an area, and roundness of the metallic region in the tomographic image, and
   the coefficient setting section sets the projection space coefficient larger and sets the image space coefficient smaller as the feature value becomes larger.

4. The medical image processing apparatus according to claim 3, wherein the feature value is obtained by using a metal image which is generated by extracting the metallic region from within the tomographic image.

5. A medical image processing apparatus which reconstructs a tomographic image from projection data of a subject in which metal material is included, comprising:
   a projection space correction section which corrects the projection data and thereby generates corrected projection data;
   an image space correction section which corrects the tomographic image by using the corrected projection data; and
   a coefficient setting section which sets a projection space coefficient which is used in the projection space correction section and an image space coefficient which is used in the image space correction section;
   wherein the coefficient setting section sets the projection space coefficient and the image space coefficient on the basis of any of a feature value of a metallic region, a scanning condition used when acquiring the projection data, and a reconstruction condition used when reconstructing the tomographic image,
   wherein the scanning condition includes a cone angle which is an opening angle in a body axis direction of the subject, and
   the coefficient setting section sets the projection space coefficient larger and sets the image space coefficient smaller as the cone angle of the projection data becomes smaller.

6. A medical image processing apparatus which reconstructs a tomographic image from projection data of a subject in which metal material is included, comprising:
   a projection space correction section which corrects the projection data and thereby generates corrected projection data;
   an image space correction section which corrects the tomographic image by using the corrected projection data; and
   a coefficient setting section which sets a projection space coefficient which is used in the projection space correction section and an image space coefficient which is used in the image space correction section;
   wherein the coefficient setting section sets the projection space coefficient and the image space coefficient on the basis of any of a feature value of a metallic region, a scanning condition used when acquiring the projection data, and a reconstruction condition used when reconstructing the tomographic image, and
   wherein the coefficient setting section sets the projection space coefficient larger and sets the image space coefficient smaller as body motion of the subject becomes smaller.

7. The medical image processing apparatus according to claim 6, wherein in a case where it is specified that a scanned region is the heart or the chest from the scanning condition and the reconstruction condition, it is decided that the body motion of the subject is large.

8. The medical image processing apparatus according to claim 6, wherein the body motion of the subject is obtained on the basis of a differential value between counter projection data which is opposed to the projection data and the projection data.

9. A medical image processing method for reconstructing a tomographic image from projection data of a subject in which metal material is included, comprising:
   a projection space correcting step of correcting the projection data and thereby generating corrected projection data;
   an image space correcting step of correcting the tomographic image by using the corrected projection data; and
   a coefficient setting step of setting a projection space coefficient which is used in the projection space correcting step and an image space coefficient which is used in the image space correcting step,
   wherein the larger the projection space coefficient is, the smaller the image space coefficient becomes.

* * * * *